(12) United States Patent
Lee et al.

(10) Patent No.: US 11,382,946 B2
(45) Date of Patent: Jul. 12, 2022

(54) MULTI-FUNCTIONAL PEPTIDES AND USE THEREOF

(71) Applicant: NOVACELL TECHNOLOGY INC., Pohang-si (KR)

(72) Inventors: Tae Hoon Lee, Seoul (KR); Jae Wang Ghim, Pohang-si (KR); Hyun Ju Lee, Seoul (KR)

(73) Assignee: NOVACELL TECHNOLOGY INC., Pohang-si (KR)

( * ) Notice: Subject to any disclaimer, the term of this patent is extended or adjusted under 35 U.S.C. 154(b) by 0 days.

(21) Appl. No.: 16/823,981

(22) Filed: Mar. 19, 2020

(65) Prior Publication Data
US 2020/0405802 A1    Dec. 31, 2020

(30) Foreign Application Priority Data

Mar. 19, 2019   (KR) .................. KR10-2019-0031330

(51) Int. Cl.
| | |
|---|---|
| *A61K 38/10* | (2006.01) |
| *A61K 38/08* | (2019.01) |
| *C07K 14/06* | (2006.01) |
| *C07K 14/08* | (2006.01) |
| *A61P 31/04* | (2006.01) |

(52) U.S. Cl.
CPC .............. *A61K 38/10* (2013.01); *A61K 38/08* (2013.01); *A61P 31/04* (2018.01); *C07K 14/06* (2013.01); *C07K 14/08* (2013.01)

(58) Field of Classification Search
CPC ......... A61K 38/10; A61K 38/08; A61P 37/02; A61P 31/04
See application file for complete search history.

(56) References Cited

U.S. PATENT DOCUMENTS

| | | |
|---|---|---|
| 2006/0229252 A1 | 10/2006 | Falla et al. |
| 2018/0319840 A1 | 11/2018 | Lee et al. |

FOREIGN PATENT DOCUMENTS

| | | |
|---|---|---|
| JP | 2008-537537 A | 9/2008 |
| JP | 2019-506362 A | 3/2019 |
| KR | 10-2007-0107748 A | 11/2007 |
| KR | 10-1855170 B1 | 5/2018 |

OTHER PUBLICATIONS

Corminboeuf et al., "FPR2/ALXR Agonists and the Resolution of Inflammation," Journal of Medicinal Chemistry, vol. 58, No. 2, pp. 537-559 (Jan. 2015) (Available online Nov. 3, 2014).

Duru et al., "Role of formic receptors in soluble urokinase receptor-induced human vascular smooth muscle migration," Journal of Surgical Research 195 (2015) 396-405 (Available online Feb. 12, 2015).

Hisaoka-Nakashima et al., "Tricyclic Antidepressant Amitriptyline-induced Glial Cell Line-derived Neurotrophic Factor Production Involves Pertussis Toxin-sensitive $G\alpha_{i}/o$ Activation in Astroglial Cells," The Journal of Biological Chemistry vol. 290, No. 22, pp. 13678-13691 (May 2015) (Available online Apr. 2015).

Mangmool et al., "$G_{i}/o$ Protein-Dependent and—Independent Actions of Pertussis Toxin (PTX)," Toxins, vol. 3, pp. 884-899 (Jul. 2011).

*Primary Examiner* — Lianko G Garyu

(74) *Attorney, Agent, or Firm* — Foley & Lardner LLP

(57) ABSTRACT

The present invention provides a novel multi-functional peptide that effectively regulates the activity of immune cells while also exhibiting excellent antibacterial activity against various bacteria such as Gram-negative bacteria and Gram-positive bacteria.

9 Claims, 2 Drawing Sheets

Specification includes a Sequence Listing.

MULTI-FUNCTIONAL PEPTIDES AND USE THEREOF

CROSS-REFERENCE TO RELATED APPLICATIONS

The present application claims priority to South Korean Patent Application No. 10-2019-0031330, filed Mar. 19, 2019.

SEQUENCE LISTING

The instant application contains a Sequence Listing which has been submitted electronically in ASCII format and is hereby incorporated by reference in its entirety. Said ASCII copy, created on Jan. 28, 2022, is named PO20-5214_sequence_2nd_amended.txt and is 10,205 bytes in size.

FIELD OF THE INVENTION

The present invention is drawn to novel multi-functional peptides and use thereof, more specifically about new multi-functional peptide and its use, which have antibacterial effects and immune cell activity control together.

BACKGROUND ART

Antimicrobial peptides are sometimes found in the nature and some synthetic peptides have been found to have antimicrobial activity. These antibacterial peptides consist of a relatively short sequence of amino acids (10 to 100 a.a.) compared to normal proteins, and when bind mainly to cell membranes 1) form ion channels in the cell membrane, which inhibit the energy generation of microorganisms, or 2) create large holes in the cell membrane, resulting in cell death. Unlike conventional antibiotics that physically destroy microorganisms, which inhibit the synthesis of microorganisms' cell walls or intracellular polymers, it has been reported that it is difficult for microorganisms to be resistant to antibacterial peptides to date. Although there are few similarities on amino acid sequence among many known antibacterial peptides to date, they show some general tendency in terms of structure or activity. For example, antibacterial peptides have positively charged amino acid such as lysine, arginine and histidine and hydrophobic region. According to Shai-Matsuzaki-Huang (SMH) model, which is currently the most feasible hypotheses related to the action mechanism of antibacterial peptides, it is explained the features in amino acid sequence and mechanism of antibacterial peptide as follows: the hydrophilic region with positive charge binds to the cell membrane of a negatively charged bacterium, and then hydrophobic region the peptide bound to the cell membrane of the bacterium interacts with hydrophobic region of phospholipid of the cell membrane and forms pores on the cell membrane and finally kill the bacterium by changing permeability of the cell membrane thereby.

Formyl peptide receptor 1 (FPR1) and formyl peptide receptor 2 (FPR2) expressed in phagocytic cells such as neutrophils and monocytes play an important roles in the defense and resolution of inflammation of host against pathogen infection (Mangmool, S. et al., *Toxins*, 3: 884-899, 2011; Corminoboeuf, O. et al., *J. Med. Chem.*, 58: 537-559, 2015). The above receptors are known to bind to pertussis toxin-sensitive Gi proteins (Nakashima, K. et al., *J. Biol. Chem.*, 290(22): 13678-13691, 2015). Among them, FPR2 is known to play an important role in inflammatory diseases. The activation of FPR2 induces the dissociation of the Gβγ subunit from the Gαi subunit and the Gβγ subunit induces the activation of phospholipase Cβ or phosphoinositide 3-kinase (Duru, E. A. et al., *J. Surg. Res.*, 195(2): 396-405, 2015). The activation of these molecules mediates various cellular reactions such as chemotactic migration, degranulation, and superoxide generation, thereby regulating immune responses in a host, and finally mediates the defense of the host against the infection of pathogens and the resolution of inflammation by inducing complex downstream signaling.

DISCLOSURE

Technical Problem

However, the present invention is intended to solve various problems, including the above problems, it is an object to provide a novel multi-functional peptide that modulates the activity of immune cells and exhibits excellent antibacterial activity against various bacteria. However, these problems are exemplary, and the scope of the present invention is not limited thereto.

Technical Solution

In an aspect of the present invention, the provided is a peptide having antibacterial and immunomodulatory activity which consists of 6 to 12 amino acids comprising an amino acid sequence selected from the group consisting of:

i) BOBWX$_1$OU; and ii) X$_1$ RWWUX$_1$X$_2$m wherein said B is a basic amino acid independently selected from the group consisting of lysine (K) and arginine (R), and said O is an aromatic amino acid independently selected from the group consisting of phenylalanine (F), tyrosine (Y), and tryptophan (W), said X$_1$ is independently selected from the group consisting of arginine (R), norleucine (Nle) or 2-naphthyl-L-alanine (Z), said U is absent or selected from the group consisting of m, X$_2$WW, RX$_2$WW and MVm, wherein said X$_2$ is norleucine (Nle), tryptophan (W) or valine (V), and said m is D-type methionine, and KFKWRYm is excluded from i).

In another aspect of the invention, the provided is an antibacterial agent comprising the above peptide as an active ingredient.

In another aspect of the present invention, the provided is an agent for treating an immune-related disease comprising the peptide as an active ingredient.

In another aspect of the present invention, the provided is a cosmetic composition for improving symptoms in a skin autoimmune disease selected from the group consisting of atopic dermatitis, lupus and psoriasis containing the peptide as an active ingredient.

Effect of the Invention

As described above, according to an embodiment of the present invention, it is possible to embody a preparation of a novel multi-functional peptide having not only high antibacterial activity against various bacteria such as Gram-negative bacteria and Gram-positive bacteria but also simultaneously controlling the activity of immune cells. However, the scope of the present invention is not limited thereto.

DETAILED DESCRIPTION OF THE INVENTION

Definition of Terms

Figure 1:
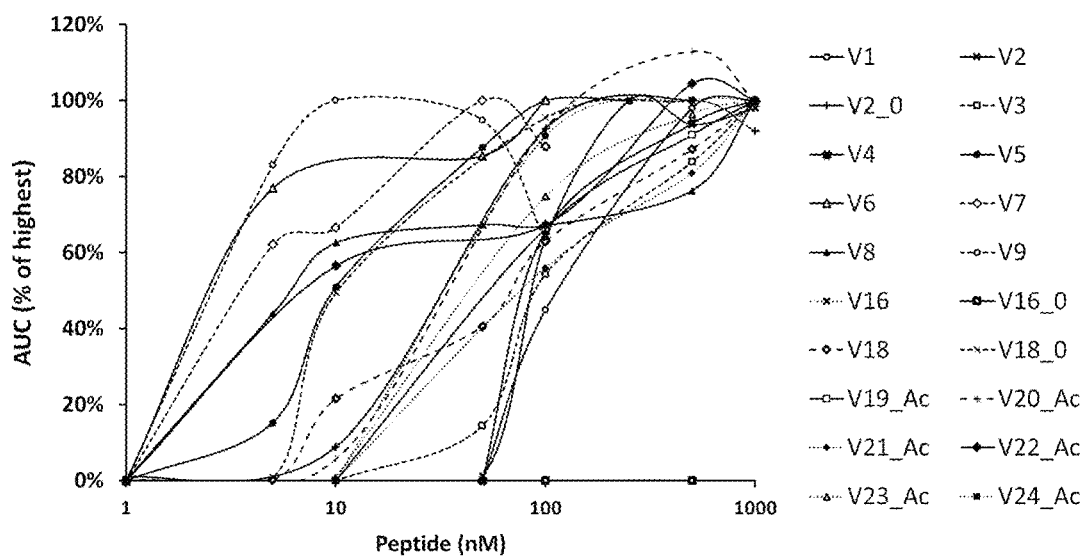
FIG. 1 is a graph showing the effect of FPR2 activation by FPR2-dependent intracellular calcium ion increase activity of the novel multi-functional peptide of the present invention.

As used herein, the term "immunomodulatory peptide" refers to a peptide that has direct or indirect antimicrobial and/or antiviral activity and immunomodulatory activity such as inflammatory response control by immune cells, immune cell migration, and inflammatory response control by epidermal or endothelial cells. In other words, the peptide plays an important role in host's defense against pathogen infection through formyl peptide receptor 1 (FPR1) and formyl peptide receptor 2 (FPR2) expressed in phagocytic cells such as neutrophils and monocytes, and epidermal cells, etc. The receptors are known to bind to pertussis toxin-sensitive Gi protein. Activation of FPR1 and FPR2 induces the dissociation of the Gβγ subunit from the Gαi subunit, and Gβγ subunit induces the activation of phospholipase Cβ or phosphoinositide 3-kinase. Activation of these molecules induces complex downstream intracellular signaling to mediate cellular responses such as chemotactic migration, degranulation, and superoxide generation.

The term "antibacterial peptide" used in this document is a cationic peptide compound, which is generally composed of a relatively simple structure, has a broad microbial spectrum including gram-positive bacteria, gram-negative bacteria, fungi, viruses, etc. Although its mechanism is not completely known, it is generally known to exhibit antibacterial activity through a mechanism of action that destroys the cell membrane of microorganisms.

BEST MODES

In an aspect of the present invention, the provided is a peptide having antibacterial and immunomodulatory activity which consists of 6 to 12 amino acids comprising an amino acid sequence selected from the group consisting of:
i) BOBWX$_1$OU; and
ii) X$_1$RWWUX$_1$X$_2$m wherein said B is a basic amino acid independently selected from the group consisting of lysine (K) and arginine (R), and said O is an aromatic amino acid independently selected from the group consisting of phenylalanine (F), tyrosine (Y), and tryptophan (W), said X$_1$ is independently selected from the group consisting of arginine (R), norleucine (Nle) or 2-naphthyl-L-alanine (Z), said U is absent or selected from the group consisting of m, X$_2$WW, RX$_2$WW and MVm, wherein said X$_2$ is norleucine (Nle), tryptophan (W) or valine (V), and said m is D-type methionine, and KFKWRYm is excluded from i).

According to the above peptide, said i) is a peptide comprising amino acid sequence selected from the group consisting of BOBW-Nle-Om, BOBWBO, BOBWZO, BOBWZOm, and BOBWBOMVm.

According to the above peptide, said ii) is a peptide comprising amino acid sequence selected from the group consisting of ZRWWX$_1$X$_2$m, RRWWX$_1$X$_2$m, and ZRWWRX$_2$WWRWm.

According to the above peptide, an octanoyl or acetyl group may be added to the N- or C-terminal of the above peptide or the C-terminal of the above peptide may be amidated.

The peptide may consist of an amino acid sequence selected from the group of SEQ ID NOs: 1 to 17.

In another aspect of the invention, the provided is an antibacterial agent comprising the above peptide as an active ingredient.

The antibacterial agent may have antibacterial activity against *P. aeruginosa* or *S. aureus*.

In another aspect of the present invention, the provided is a pharmaceutical composition for treating an immune-related disease comprising the peptide as an active ingredient.

According to the pharmaceutical composition, the immune-related disease may be atopic dermatitis, psoriasis, conjunctivitis, keratitis, dry eye syndrome, pneumonia, asthma, rheumatoid arthritis, ankylosing spondylitis, ulcerative colitis or Crohn's disease.

In another aspect of the present invention, the provided is a cosmetic composition for improving symptoms in a skin autoimmune disease selected from the group consisting of atopic dermatitis, lupus and psoriasis containing the peptide as an active ingredient.

The pharmaceutical composition comprising the peptide as an active ingredient may include at least one of pharmaceutical diluents selected from saline, buffered saline, dextrose, water, glycerol and ethanol, but the diluent is not limited thereto. The pharmaceutical composition may be applied differently depending on the purpose of administration and status of disease. The amount of active ingredient that is actually administered should be determined considering a variety of related factors such as the disease to be treated, the extent of the patient's condition, co-administration with other agents (e.g. chemotherapeutic agents), patient's age, gender, weight, food, administration time, route of administration, and dosage ratio of the composition. The composition may be administered once or 1-3 times a day, although the dosage and administration route may be adjusted according to the type and severity of the disease.

The pharmaceutical composition comprising the peptide as an active ingredient may be prepared in any formulation conventionally prepared in the art (eg, Remington's Pharmaceutical Science, latest edition; Mack Publishing Company, Easton Pa.), and the form of the formulation may preferably be an external preparation but not limited thereto. The external preparations of the present invention include conventional external preparations such as sheet, liquid coating, spray, lotion, cream, poultice, powder, penetrating pad, spray, gel including hydrogel, paste, liniment, ointment, aerosol, suspension and percutaneous absorbent. These formulations are described in Remington's Pharmaceutical Science, 15th Edition, 1975, Mack Publishing Company, Easton, Pa. 18042 (Chapter 87: Blaug, Seymour), a prescription generally known to all pharmaceutical chemistries.

The pharmaceutical compositions comprising the peptide or substances of the invention can be administered orally or parenterally. Parenteral administration means administration of the drug through a route other than oral administration, i.e., intrarectal, intravenous, intraperitoneal, intramuscular, intraarterial, transdermal, inhalation, intraocular, and subcutaneous. The pharmaceutical composition comprising the peptide or substance can be formulated in any form, such as oral dosage form, injectable solution or topical preparation. Formulations are preferably prepared for oral and injectable administration (true solutions, suspensions or emulsions), and are most preferably prepared in oral form such as tablets, capsules, soft capsules, aqueous pharmaceuticals, pills, granules, etc. desirable. In the above formulation, the peptide of the present invention is filled into a soft capsule without excipient, and is made into a suitable formulation after being mixed or diluted with a carrier. Examples of suitable carriers include starch, water, brine, Ringer's solution, and dextrose.

The cosmetic composition comprising the peptide of the present invention as an active ingredient may include one or more additives used in the formulation of the cosmetic composition. For example, such additives include 1, 3-butylene glycol, soybean phospholipid choline, sphingosine, cholesterol, Tween 80, phytosphingosine, salicylic acid, skin moisturizers (wetting agents), softeners, natural oils, natural extracts, keratin, lipoids, Absorbent water-soluble substances, stratum corneum ceramides, epidermal lipid acidic membrane fatty acids, cholesteryl esters, ethanol, distilled water, and the like.

The pharmaceutical composition comprising the peptide of the present invention as an active ingredient can be administered through oral administration or parenteral administration, oral administration is more preferred, but is not limited thereto. When administered parenterally, it is possible to administer via various routes such as intravenous injection, intranasal inhalation, intramuscular administration, intraperitoneal administration, and percutaneous absorption.

In addition, the pharmaceutical composition comprising the peptide of the present invention as an active ingredient may be administered in a dose of 0.1 mg/kg to 1 g/kg, more preferably in a dosage of 1 mg/kg to 600 mg/kg Is administered. Meanwhile, the dosage may be appropriately adjusted according to the patient's age, gender and condition.

MODE FOR THE INVENTION

Hereinafter, the present invention will be described in more detail through examples and experimental examples. However, the present invention is not limited to the examples and experimental examples disclosed below, and can be implemented in various different ways, and the following examples and experimental examples make the disclosure of the present invention completely and inform a skilled in the art the full scope of the invention perfectly.

Example 1: Preparation of Antibacterial Peptide

The present inventors developed a peptide (KFKWRYm) having antibacterial activity through a conventional basic screening research and had patented the peptide (Korea Patent No. 10-1855170). Subsequently, in order to develop an improved peptide having better antimicrobial and immunomodulatory function than the peptide, the present inventors designed various variants of the patented peptide whose amino acid sequenced varied and synthesized various antibacterial candidate peptides using a general amino acid synthesis method (Umbarger, H E, $Ann.\ Rev.\ Biochem.,$ 47: 533-606, 1978).

In addition, the present inventors added a modification in the form of adding an octanoyl group or an acetyl group to the N-terminus of the peptides synthesized above and/or substituting an amine group for the C-terminal carboxyl group.

Experimental Example 1: Analysis of FPR2 Activation Effect of Novel Peptides

The present inventors observed a change in calcium ion permeability of the candidate peptides according to an embodiment of the present invention in order to determine whether they can activate the immunomodulatory function in a body or not. Particularly, intracellular concentration of calcium ions was measured to confirm that the peptide activates FPR2. RBL cells that do neither express FPR1 nor FPR2, RBL cells overexpressed FPR1 (FPR1-RBL) and RBL cells that overexpressed FPR2 (FPR2-RBL) were used and Fura-2/AM which is a fluorophore having high binding affinity to calcium in order to measure intracellular calcium ion level sensitively. For this purpose, cells were cultured in RPMI medium supplemented with 10% fetal bovine serum and harvested by centrifugation in log phase (mid-log phase, $1-3\times10^7$ cells/ml), and then washed several times with RPMI medium not supplemented with fetal bovine serum, and then the cells were resuspended in RPMI medium to $1\times10^7$ cells/ml. Subsequently, a final 3 μM concentration of Fura-2/AM was added and the cells were incubated for 45 minutes in a 37° C., 5% $CO_2$ incubator. After the appropriated time, the cells are harvested, washed again with RPMI medium, and then suspended in the appropriate amount of RPMI medium supplemented with 250 μM of sulfinpyrazone, in order to prevent loss of Fura-2 entering the cells. About $2\times10^6$ cells were taken each time, harvested by rapid centrifugation, and resuspended in 1 ml of a Locke solution without addition of calcium ions and EGTA added, and the ratio of absorbance at two wavelengths of 340 nm and 380 nm on a spectrophotometer were monitored by treating the peptides according to an embodiment of the present invention at different concentrations (1 µM, 0.1 µM, and 0.01 µM) at intervals of about 1 minute, and then the difference in absorbance at two wavelengths was investigated. It was converted to the concentration of free calcium ions into cells according to the method of Grynkiewicz.

As a result, it showed FPR2 activation effect in most of the peptides, which suggests that the peptide according to an embodiment of the present invention can modulate the immune function of an individual through binding and activation to FPR2 (FIG. 1). The results of analyzing the FPR2 activation effect of the peptides are summarized in Table 1 below.

TABLE 1

Analysis on FPR2 activity of the tested peptides

| Peptide | FPR2 activity ($EC_{50}$, nm) | SEQ ID Nos |
|---|---|---|
| V3 | 106.9 | 1 |
| V4 | 64.0 | 2 |
| V5 | 41.5 | 3 |
| V6 | 4.2 | 4 |
| V7 | 3.2 | 5 |
| V8 | 6.4 | 6 |
| V9 | 4.7 | 7 |
| V16 | — | 8 |
| V16_0 | — | 9 |
| V18 | 62.8 | 10 |
| V18_0 | 10.0 | 11 |
| V19_Ac | 69.4 | 12 |
| V20_Ac | 45.3 | 13 |
| V21_Ac | 92.3 | 14 |
| V22_Ac | 16.2 | 15 |

TABLE 1-continued

Analysis on FPR2 activity of the tested peptides

| Peptide | FPR2 activity ($EC_{50}$, nm) | SEQ ID Nos |
|---|---|---|
| V23_Ac | 61.3 | 16 |
| V24_Ac | 58.6 | 17 |

Experimental Example 2: Antibacterial Activity Test of New Peptide

The present inventors evaluated FPR2 activation ability in order to select peptides showing excellent performance among various peptides synthesized in the Example 1. Particularly, in order to measure the antimicrobial activity of the peptide, after preparing Gram-positive bacteria *Staphylococcus aureus* (*S. aureus*) and Gram-negative bacteria *Pseudomonas aeruginosa* (*P. aeruginosa*), the bacteria were plated on agar plate medium by fourth streaking and cultured overnight in a 36° C. incubator. The next day, the strain colonies produced on the agar plate medium were inoculated into 3 ml nutrient medium and cultured overnight in a stirring incubator at 36° C. and 220 rpm. The next day, the bacteria were diluted to measure absorbance at 600 nm, adjusted to $OD_{600}$=0.5, and diluted in a 1:100 ratio in nutrient medium. Then, the peptides prepared in the above Examples were serially diluted in concentrations of 0, 1.25, 2.5, 5, 10, and 20 µM in a nutrient medium to prepare 1 ml each, and then inoculated with 1 ml of the diluted bacteria. Subsequently, the mixture was stirred under conditions of 36° C. and 220 rpm, and incubated for 18 hours, and absorbance at 600 nm was measured.

Figure 2:
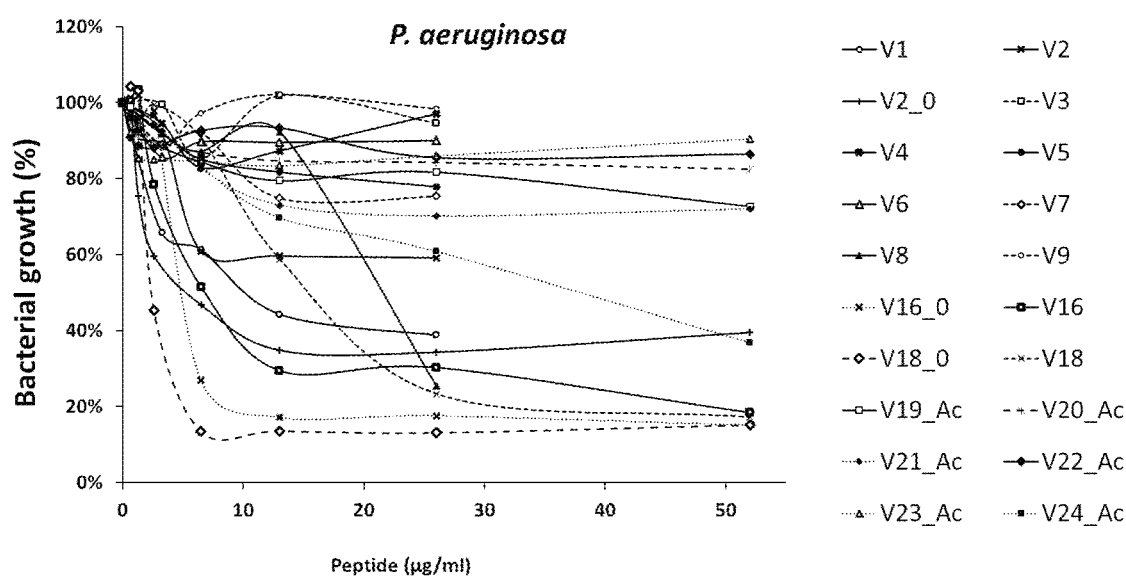
FIG. 2 is a graph showing the antibacterial activity of the novel multi-functional peptide of the present invention against *P. aeruginosa*.
Figure 3:
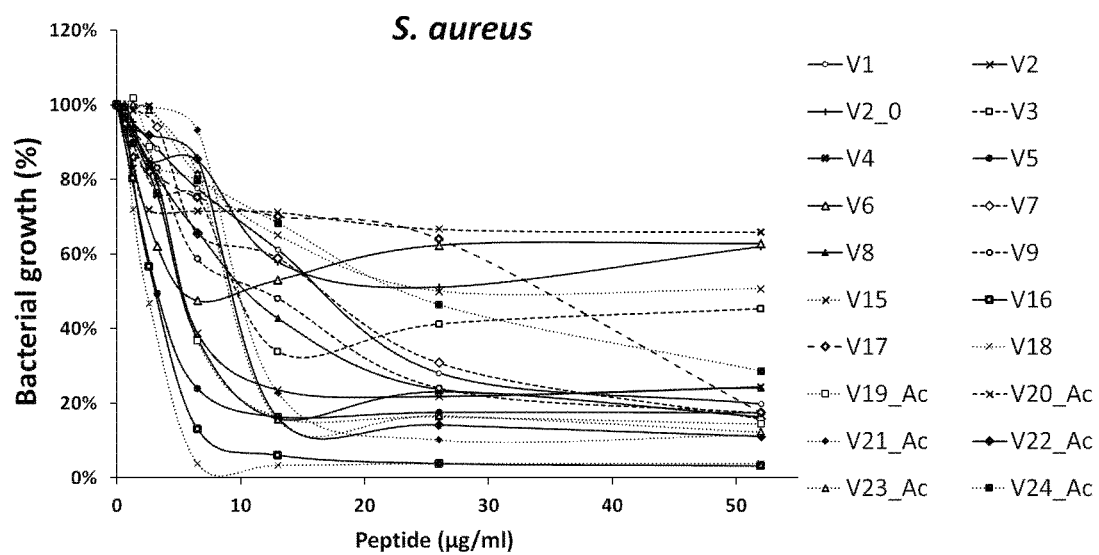
FIG. 3 is a graph showing the antibacterial activity of the novel multi-functional peptide of the present invention against *S. aureus*.

As a result, 20 peptides showing high antibacterial activity against *P. aeruginosa* and *S. aureus*) were selected (FIGS. 2 and 3). The sequence information and antibacterial activity for the peptides are summarized in Table.

TABLE 2

Amino acid sequence information and antibacterial activity of the antibacterial peptide of the present invention

| Peptide | Amino acid sequence | M.W. | Antimicrobial activity ($IC_{50}$, µg/ml) P. aeruginosa | S. aureus |
|---|---|---|---|---|
| V3 | Oct-KFKW-Nle-Ym-$NH_2$ | 1,140.5 | — | 15.2 |
| V4 | Oct-KWKW-Nle-Ym-$NH_2$ | 1,179.5 | — | 5.1 |
| V5 | Oct-RWRW-Nle-Ym-$NH_2$ | 1,235.6 | >50 | 2.0 |
| V6 | Oct-KFKWRYMVm-$NH_2$ | 1,413.8 | — | >50 |
| V7 | Oct-RWRWRYMVm-$NH_2$ | 1,452.9 | >50 | 16.3 |
| V8 | Oct-RWRWRYMVm-$NH_2$ | 1,508.9 | 24.4 | 13.0 |
| V9 | Oct-RWRWRWMVm-$NH_2$ | 1,532.0 | — | 12.7 |
| V16 | Oct-RWRWZW-$NH_2$ | 1,211.4 | 7.3 | 2.7 |
| V16_0 | RWRWZW-$NH_2$ | 1,085.2 | 4.3 | 30.2 |
| V18 | Oct-RWRWZWm-$NH_2$ | 1,342.6 | 16.2 | 2.3 |
| V18_0 | RWRWZWm-$NH_2$ | 1,216.4 | 21.1 | 6.8 |
| V19_Ac | Ac-ZRWWRWm-$NH_2$ | 1,258.5 | >50 | 5.4 |
| V20_Ac | Ac-ZRWW-Nle-Wm-$NH_2$ | 1,215.4 | >50 | >50 |
| V21_Ac | Ac-ZRWWRVm-$NH_2$ | 1,171.4 | >50 | 9.4 |
| V22_Ac | Ac-ZRWWRVWWRWm-$NH_2$ | 1,886.2 | >50 | 13.6 |
| V23_Ac | Ac-ZRWWR-Nle-WWRWm-$NH_2$ | 1,900.2 | >50 | 13.3 |
| V24_Ac | Ac-RRWWRWm-$NH_2$ | 1,217.5 | 47.8 | 24.0 |

The present invention has been described with reference to the above-described Examples and Experimental Examples, but it is understood that these are merely exemplary, and various modifications and equivalent other Examples and Experimental Examples are possible to those skilled in the art. Therefore, the true scope of the present invention should be determined by the technical spirit of the appended claims.

The invention claimed is:

1. A peptide having antibacterial and immunomodulatory activity which consists of 7 to 12 amino acids comprising an amino acid sequence selected from the group consisting of:
 i) BOBW-NleOm (SEQ ID NO: 18), BOBWZOm (SEQ ID NO: 20), and BOBWBOMVm (SEQ ID NO: 21); and
 ii) ZRWWX$_1$X$_2$m (SEQ ID NO: 22), RRWWX$_1$X$_2$m (SEQ ID NO: 23), and ZRWWRX$_2$WWRWm (SEQ ID NO: 24);
 wherein:
 B is a basic amino acid independently selected from the group consisting of lysine (K) and arginine (R);
 O is an aromatic amino acid independently selected from the group consisting of phenylalanine (F), tyrosine (Y), and tryptophan (W);
 X$_1$ is independently selected from the group consisting of arginine (R), norleucine (Nle), and 2-naphthyl-L-alanine (Z);
 X$_2$ is independently selected from the group consisting of norleucine (Nle), tryptophan (W), and valine (V);
 m is D-type methionine, and
 Z is 2-naphthyl-L-alanine.

2. The peptide according to claim 1, wherein the peptide further comprises an N-terminal or C-terminal octanoyl or acetyl group.

3. The peptide according to claim 1, wherein the C-terminal of the peptide is amidated.

4. The peptide according to claim 1, wherein the peptide consists of an amino acid sequence selected from the group consisting of SEQ ID. NOs: 1 to 7 and 10 to 17.

5. An antibacterial agent comprising the peptide according to claim 1 as an active ingredient.

6. The antibacterial agent according to claim 5, wherein the peptide has antibacterial activity against *P. aeruginosa* or *S. aureus*.

7. A pharmaceutical composition for treating immune-related disease comprising the peptide according to claim 1 as an active ingredient.

8. The pharmaceutical composition of claim 7, wherein the immune-related disease is atopic dermatitis, psoriasis, conjunctivitis, keratitis, dry eye syndrome, pneumonia, asthma, rheumatoid arthritis, ankylosing spondylitis, ulcerative colitis or Crohn's disease.

9. A cosmetic composition for improving symptoms in a skin autoimmune disease selected from the group consisting of atopic dermatitis, lupus and psoriasis containing the peptide according to claim 1 as an active ingredient.

\* \* \* \* \*

```
                          SEQUENCE LISTING

<160> NUMBER OF SEQ ID NOS: 25

<210> SEQ ID NO 1
<211> LENGTH: 7
<212> TYPE: PRT
<213> ORGANISM: Artificial Sequence
<220> FEATURE:
<223> OTHER INFORMATION: V3
<220> FEATURE:
<221> NAME/KEY: VARIANT
<222> LOCATION: (5)
<223> OTHER INFORMATION: Xaa is Nle
<220> FEATURE:
<221> NAME/KEY: VARIANT
<222> LOCATION: (7)
<223> OTHER INFORMATION: Xaa is D-type methionine

<400> SEQUENCE: 1

Lys Phe Lys Trp Xaa Tyr Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: V4
<220> FEATURE:
<221> NAME/KEY: VARIANT
<222> LOCATION: (5)
<223> OTHER INFORMATION: Xaa is Nle
<220> FEATURE:
<221> NAME/KEY: VARIANT
<222> LOCATION: (7)
<223> OTHER INFORMATION: Xaa is D-type methionine

<400> SEQUENCE: 2

Lys Trp Lys Trp Xaa Tyr Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: V5
<220> FEATURE:
<221> NAME/KEY: VARIANT
<222> LOCATION: (5)
<223> OTHER INFORMATION: Xaa is Nle
<220> FEATURE:
<221> NAME/KEY: VARIANT
<222> LOCATION: (7)
<223> OTHER INFORMATION: Xaa is D-type methionine

<400> SEQUENCE: 3

Arg Trp Arg Trp Xaa Tyr Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: V6
<220> FEATURE:
```

-continued

```
<221> NAME/KEY: VARIANT
<222> LOCATION: (9)
<223> OTHER INFORMATION: Xaa is D-type methionine

<400> SEQUENCE: 4

Lys Phe Lys Trp Arg Tyr Met Val Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: V7
<220> FEATURE:
<221> NAME/KEY: VARIANT
<222> LOCATION: (9)
<223> OTHER INFORMATION: Xaa is D-type methionine

<400> SEQUENCE: 5

Arg Trp Arg Trp Arg Tyr Met Val Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: V8
<220> FEATURE:
<221> NAME/KEY: VARIANT
<222> LOCATION: (9)
<223> OTHER INFORMATION: Xaa is D-type methionine

<400> SEQUENCE: 6

Arg Trp Arg Trp Arg Tyr Met Val Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: V9
<220> FEATURE:
<221> NAME/KEY: VARIANT
<222> LOCATION: (9)
<223> OTHER INFORMATION: Xaa is D-type methionine

<400> SEQUENCE: 7

Arg Trp Arg Trp Arg Trp Met Val Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: V16
<220> FEATURE:
<221> NAME/KEY: VARIANT
<222> LOCATION: (5)
<223> OTHER INFORMATION: Xaa is 2-naphthyl-L-alanine

<400> SEQUENCE: 8

Arg Trp Arg Trp Xaa Trp
1               5

<210> SEQ ID NO 9
```

```
<211> LENGTH: 6
<212> TYPE: PRT
<213> ORGANISM: Artificial Sequence
<220> FEATURE:
<223> OTHER INFORMATION: V16_0
<220> FEATURE:
<221> NAME/KEY: VARIANT
<222> LOCATION: (5)
<223> OTHER INFORMATION: Xaa is 2-naphthyl-L-alanine

<400> SEQUENCE: 9

Arg Trp Arg Trp Xaa Trp
1               5

<210> SEQ ID NO 10
<211> LENGTH: 7
<212> TYPE: PRT
<213> ORGANISM: Artificial Sequence
<220> FEATURE:
<223> OTHER INFORMATION: V18
<220> FEATURE:
<221> NAME/KEY: VARIANT
<222> LOCATION: (5)
<223> OTHER INFORMATION: Xaa is 2-naphthyl-L-alanine
<220> FEATURE:
<221> NAME/KEY: VARIANT
<222> LOCATION: (7)
<223> OTHER INFORMATION: Xaa is D-type methionine

<400> SEQUENCE: 10

Arg Trp Arg Trp Xaa Trp Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: V18_0
<220> FEATURE:
<221> NAME/KEY: VARIANT
<222> LOCATION: (5)
<223> OTHER INFORMATION: Xaa is 2-naphthyl-L-alanine
<220> FEATURE:
<221> NAME/KEY: VARIANT
<222> LOCATION: (7)
<223> OTHER INFORMATION: Xaa is D-type methionine

<400> SEQUENCE: 11

Arg Trp Arg Trp Xaa Trp Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: V19_Ac
<220> FEATURE:
<221> NAME/KEY: VARIANT
<222> LOCATION: (1)
<223> OTHER INFORMATION: Xaa is 2-naphthyl-L-alanine
<220> FEATURE:
<221> NAME/KEY: VARIANT
<222> LOCATION: (7)
<223> OTHER INFORMATION: Xaa is D-type methionine

<400> SEQUENCE: 12

Xaa Arg Trp Trp Arg Trp Xaa
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: V20_Ac
<220> FEATURE:
<221> NAME/KEY: VARIANT
<222> LOCATION: (1)
<223> OTHER INFORMATION: Xaa is 2-naphthyl-L-alanine
<220> FEATURE:
<221> NAME/KEY: VARIANT
<222> LOCATION: (5)
<223> OTHER INFORMATION: Xaa is Nle
<220> FEATURE:
<221> NAME/KEY: VARIANT
<222> LOCATION: (7)
<223> OTHER INFORMATION: Xaa is D-type methionine

<400> SEQUENCE: 13

Xaa Arg Trp Trp Xaa Trp Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: V21_Ac
<220> FEATURE:
<221> NAME/KEY: VARIANT
<222> LOCATION: (1)
<223> OTHER INFORMATION: Xaa is 2-naphthyl-L-alanine
<220> FEATURE:
<221> NAME/KEY: VARIANT
<222> LOCATION: (7)
<223> OTHER INFORMATION: Xaa is D-type methionine

<400> SEQUENCE: 14

Xaa Arg Trp Trp Arg Val Xaa
1               5

<210> SEQ ID NO 15
<211> LENGTH: 11
<212> TYPE: PRT
<213> ORGANISM: Artificial Sequence
<220> FEATURE:
<223> OTHER INFORMATION: V22_Ac
<220> FEATURE:
<221> NAME/KEY: VARIANT
<222> LOCATION: (1)
<223> OTHER INFORMATION: Xaa is 2-naphthyl-L-alanine
<220> FEATURE:
<221> NAME/KEY: VARIANT
<222> LOCATION: (11)
<223> OTHER INFORMATION: Xaa is D-type methionine

<400> SEQUENCE: 15

Xaa Arg Trp Trp Arg Val Trp Trp Arg Trp Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: V23_Ac
<220> FEATURE:
<221> NAME/KEY: VARIANT
<222> LOCATION: (1)
<223> OTHER INFORMATION: Xaa is 2-naphthyl-L-alanine
<220> FEATURE:
<221> NAME/KEY: VARIANT
```

```
<222> LOCATION: (6)
<223> OTHER INFORMATION: Xaa is Nle
<220> FEATURE:
<221> NAME/KEY: VARIANT
<222> LOCATION: (11)
<223> OTHER INFORMATION: Xaa is D-type methionine

<400> SEQUENCE: 16

Xaa Arg Trp Trp Arg Xaa Trp Trp Arg Trp Xaa
1               5                   10

<210> SEQ ID NO 17
<211> LENGTH: 7
<212> TYPE: PRT
<213> ORGANISM: Artificial Sequence
<220> FEATURE:
<223> OTHER INFORMATION: V24_Ac
<220> FEATURE:
<221> NAME/KEY: VARIANT
<222> LOCATION: (7)
<223> OTHER INFORMATION: Xaa is D-type methionine

<400> SEQUENCE: 17

Arg Arg Trp Trp Arg Trp Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (1)
<223> OTHER INFORMATION: Xaa is lysine (K) or arginine (R)
<220> FEATURE:
<221> NAME/KEY: VARIANT
<222> LOCATION: (2)
<223> OTHER INFORMATION: Xaa is phenylalanine (F), tyrosine (Y) or
     tryptophan (W)
<220> FEATURE:
<221> NAME/KEY: VARIANT
<222> LOCATION: (3)
<223> OTHER INFORMATION: Xaa is lysine (K) or arginine (R)
<220> FEATURE:
<221> NAME/KEY: VARIANT
<222> LOCATION: (5)
<223> OTHER INFORMATION: Xaa is norleucine (Nle)
<220> FEATURE:
<221> NAME/KEY: VARIANT
<222> LOCATION: (6)
<223> OTHER INFORMATION: Xaa is phenylalanine (F), tyrosine (Y) or
     tryptophan (W)
<220> FEATURE:
<221> NAME/KEY: VARIANT
<222> LOCATION: (7)
<223> OTHER INFORMATION: D-methionine

<400> SEQUENCE: 18

Xaa Xaa Xaa Trp Xaa Xaa Met
1               5

<210> SEQ ID NO 19
<211> LENGTH: 7
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (1)
<223> OTHER INFORMATION: Xaa is lysine (K) or arginine (R)
```

-continued

```
<220> FEATURE:
<221> NAME/KEY: VARIANT
<222> LOCATION: (2)
<223> OTHER INFORMATION: Xaa is phenylalanine (F), tyrosine (Y) or
      tryptophan (W)
<220> FEATURE:
<221> NAME/KEY: VARIANT
<222> LOCATION: (3)
<223> OTHER INFORMATION: Xaa is lysine (K) or arginine (R)
<220> FEATURE:
<221> NAME/KEY: VARIANT
<222> LOCATION: (5)
<223> OTHER INFORMATION: Xaa is lysine (K) or arginine (R)
<220> FEATURE:
<221> NAME/KEY: VARIANT
<222> LOCATION: (6)
<223> OTHER INFORMATION: Xaa is phenylalanine (F), tyrosine (Y) or
      tryptophan (W)
<220> FEATURE:
<221> NAME/KEY: VARIANT
<222> LOCATION: (7)
<223> OTHER INFORMATION: D-methionine

<400> SEQUENCE: 19

Xaa Xaa Xaa Trp Xaa Xaa Met
1               5

<210> SEQ ID NO 20
<211> LENGTH: 7
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (1)
<223> OTHER INFORMATION: Xaa is lysine (K) or arginine (R)
<220> FEATURE:
<221> NAME/KEY: VARIANT
<222> LOCATION: (2)
<223> OTHER INFORMATION: Xaa is phenylalanine (F), tyrosine (Y) or
      tryptophan (W)
<220> FEATURE:
<221> NAME/KEY: VARIANT
<222> LOCATION: (3)
<223> OTHER INFORMATION: Xaa is lysine (K) or arginine (R)
<220> FEATURE:
<221> NAME/KEY: VARIANT
<222> LOCATION: (5)
<223> OTHER INFORMATION: Xaa is 2-naphthyl-L-alanine (Z)
<220> FEATURE:
<221> NAME/KEY: VARIANT
<222> LOCATION: (6)
<223> OTHER INFORMATION: Xaa is phenylalanine (F), tyrosine (Y) or
      tryptophan (W)
<220> FEATURE:
<221> NAME/KEY: VARIANT
<222> LOCATION: (7)
<223> OTHER INFORMATION: D-methionine

<400> SEQUENCE: 20

Xaa Xaa Xaa Trp Xaa Xaa Met
1               5

<210> SEQ ID NO 21
<211> LENGTH: 9
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (1)
<223> OTHER INFORMATION: Xaa is lysine (K) or arginine (R)
<220> FEATURE:
```

```
<221> NAME/KEY: VARIANT
<222> LOCATION: (2)
<223> OTHER INFORMATION: Xaa is phenylalanine (F), tyrosine (Y) or
      tryptophan (W)
<220> FEATURE:
<221> NAME/KEY: VARIANT
<222> LOCATION: (3)
<223> OTHER INFORMATION: Xaa is lysine (K) or arginine (R)
<220> FEATURE:
<221> NAME/KEY: VARIANT
<222> LOCATION: (5)
<223> OTHER INFORMATION: Xaa is lysine (K) or arginine (R)
<220> FEATURE:
<221> NAME/KEY: VARIANT
<222> LOCATION: (6)
<223> OTHER INFORMATION: Xaa is phenylalanine (F), tyrosine (Y) or
      tryptophan (W)
<220> FEATURE:
<221> NAME/KEY: VARIANT
<222> LOCATION: (9)
<223> OTHER INFORMATION: D-methionine

<400> SEQUENCE: 21

Xaa Xaa Xaa Trp Xaa Xaa Met Val Met
1               5

<210> SEQ ID NO 22
<211> LENGTH: 7
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (1)
<223> OTHER INFORMATION: Xaa is 2-naphthyl-L-alanine (Z)
<220> FEATURE:
<221> NAME/KEY: VARIANT
<222> LOCATION: (5)
<223> OTHER INFORMATION: Xaa is arginine (R), norleucine (Nle),
      2-naphthyl-L-alanine (Z)
<220> FEATURE:
<221> NAME/KEY: VARIANT
<222> LOCATION: (6)
<223> OTHER INFORMATION: Xaa is norleucine (Nle), tryptophan (W), or
      valine (V)
<220> FEATURE:
<221> NAME/KEY: VARIANT
<222> LOCATION: (7)
<223> OTHER INFORMATION: D-methionine

<400> SEQUENCE: 22

Xaa Arg Trp Trp Xaa Xaa Met
1               5

<210> SEQ ID NO 23
<211> LENGTH: 7
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (5)
<223> OTHER INFORMATION: Xaa is arginine (R), norleucine (Nle) or
      2-naphthyl-L-alanine (Z)
<220> FEATURE:
<221> NAME/KEY: VARIANT
<222> LOCATION: (6)
<223> OTHER INFORMATION: Xaa is norleucine (Nle), tryptophan (W) or
      valine (V)
<220> FEATURE:
<221> NAME/KEY: VARIANT
<222> LOCATION: (7)
<223> OTHER INFORMATION: D-methionine
```

```
<400> SEQUENCE: 23

Arg Arg Trp Trp Xaa Xaa Met
1               5

<210> SEQ ID NO 24
<211> LENGTH: 11
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (1)
<223> OTHER INFORMATION: Xaa is 2-naphthtyl-L-alanine (Z)
<220> FEATURE:
<221> NAME/KEY: VARIANT
<222> LOCATION: (6)
<223> OTHER INFORMATION: Xaa is norleucine (Nle), tryptophan (W) or
      valine (V)
<220> FEATURE:
<221> NAME/KEY: VARIANT
<222> LOCATION: (11)
<223> OTHER INFORMATION: D-methionine

<400> SEQUENCE: 24

Xaa Arg Trp Trp Arg Xaa Trp Trp Arg Trp Met
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Immunomodulatory peptide
<220> FEATURE:
<221> NAME/KEY: VARIANT
<222> LOCATION: (7)
<223> OTHER INFORMATION: D-methionine

<400> SEQUENCE: 25

Lys Phe Lys Trp Arg Tyr Met
1               5
```